(12) United States Patent
Berentsveig et al.

(10) Patent No.: US 9,358,315 B2
(45) Date of Patent: Jun. 7, 2016

(54) SUB-CYCLE BASED AEROSOL DISINFECTION SYSTEM

(75) Inventors: Vladimir Berentsveig, Alexandria (AU); Ron Weinberger, Alexandria (AU); Michael Potas, Alexandria (AU)

(73) Assignee: SABAN VENTURES PTY LIMITED, New South Wales (AU)

( * ) Notice: Subject to any disclaimer, the term of this patent is extended or adjusted under 35 U.S.C. 154(b) by 1042 days.

(21) Appl. No.: 13/000,496

(22) PCT Filed: Jun. 30, 2009

(86) PCT No.: PCT/AU2009/000843
§ 371 (c)(1),
(2), (4) Date: Mar. 29, 2011

(87) PCT Pub. No.: WO2010/000022
PCT Pub. Date: Jan. 7, 2010

(65) Prior Publication Data
US 2011/0165021 A1    Jul. 7, 2011

(30) Foreign Application Priority Data

Jun. 30, 2008    (AU) ................. 2008903323

(51) Int. Cl.
*A61L 2/18* (2006.01)
*A61L 2/22* (2006.01)
(Continued)

(52) U.S. Cl.
CPC . *A61L 2/186* (2013.01); *A61L 2/22* (2013.01); *A61L 2/26* (2013.01); *A61L 11/00* (2013.01); *A61L 2202/122* (2013.01); *A61L 2202/14* (2013.01)

(58) Field of Classification Search
CPC ...... A61L 2/186; A61L 2/22; A61L 2202/122
USPC ....................................... 422/28, 3
See application file for complete search history.

(56) References Cited

U.S. PATENT DOCUMENTS 6,475,435 B1 * 11/2002 Taggart ........................ 422/33
6,500,465 B1    12/2002 Ronlan
(Continued)

FOREIGN PATENT DOCUMENTS

AU    2006249279 A1    1/2007
EP    0 411 970 A1    2/1991
(Continued)

OTHER PUBLICATIONS

International Search Report in International Application No. PCT/AU2009/000843; Mailing Date: Jul. 23, 2009.
(Continued)

*Primary Examiner* — Kevin Joyner
(74) *Attorney, Agent, or Firm* — Finnegan, Henderson, Farbow, Garrett & Dunner, LLP

(57) ABSTRACT

A method of sterilizing an object comprising the steps of i) placing an article to be sterilized in a sterilization chamber; ii) providing a sterilizing mist (for example hydrogen peroxide solution) to the sterilization chamber, thereby to contact said article for a first duration; iii) providing a gas flow to said chamber for a second duration, thereby to displace, where present, said sterilizing mist and to remove, where present, condensed mist from said article; wherein the total reduction in micro organisms over a time period encompassing the first duration and the second duration is less than log 6; and wherein steps ii) and iii) are repeated at least once to achieve a predetermined sterilization parameter such as a predetermined sum total of contact time between the sterilizing mist and the article, a predetermined sum total of sterilizing mist provided to the sterilization chamber or a predetermined level of sterilization.

27 Claims, 5 Drawing Sheets

(51) Int. Cl.
*A61L 2/26* (2006.01)
*A61L 11/00* (2006.01)

(56) References Cited

U.S. PATENT DOCUMENTS

| | | | |
|---|---|---|---|
| 6,645,429 B1* | 11/2003 | Raniwala | 422/28 |
| 2003/0086820 A1* | 5/2003 | McDonnell et al. | 422/28 |
| 2003/0143110 A1 | 7/2003 | Kritzler et al. | |
| 2007/0065335 A1 | 3/2007 | Bedard et al. | |

FOREIGN PATENT DOCUMENTS

| | | |
|---|---|---|
| EP | 1 283 061 A1 | 2/2003 |
| GB | 2223678 A | 4/1990 |
| JP | 2003-327216 | 11/2003 |
| JP | 2005-58495 A | 3/2005 |
| JP | 2005-143726 A | 6/2005 |
| JP | 2005-205067 A | 8/2005 |
| JP | 2009-502369 | 1/2009 |
| JP | 2009-502489 | 1/2009 |
| KR | 100782040 B1 | 12/2007 |
| WO | WO-2007/014435 A1 | 2/2007 |
| WO | WO 2007/014436 A1 | 2/2007 |
| WO | WO 2007/014437 A1 | 2/2007 |
| WO | WO 2007/014438 A1 | 2/2007 |
| WO | WO 2008/021481 A2 | 2/2008 |

OTHER PUBLICATIONS

Response to Written Opinion in International Application No. PCT/AU2009/000843; Mar. 2, 2010.
International Preliminary Report on Patentability in International Application No. PCT/AU2009/000843; Mailing Date: Mar. 15, 2010.
Office Action dated Jan. 31, 2013 in corresponding Chinese Patent Application No. 200980126082.1, with English translation, 14 pages.
Supplemental EP Search Report for related EP Application 09771839, dated Jul. 25, 2011 (4 pages).
Japanese Patent Office, Notification of Reasons for Rejection in corresponding Japanese Application No. JP 2011-515024 and English translation thereof, Nov. 11, 2014, 4 pages.

* cited by examiner time $t_n$  $t_m$ aerosol flow into chamber total aerosol flow into chamber aerosol present in chamber

Fig. 3a time max
min $t_n$  $t_m$ aerosol flow into chamber total aerosol flow into chamber aerosol present in chamber

Fig. 3c

SUB-CYCLE BASED AEROSOL DISINFECTION SYSTEM

CROSS-REFERENCE TO RELATED APPLICATIONS

This application is a national phase application of International Application No. PCT/AU2009/000843, filed Jun. 30, 2009, and claims the priority of Australian Application No. 2008903323, filed Jun. 30, 2008, the contents of both of which are incorporated herein by reference.

FIELD OF THE INVENTION

The invention relates to methods and apparatus for sterilisation which employ the cyclical application and removal of aerosols.

BACKGROUND OF THE INVENTION

Any discussion of the prior art throughout the specification should in no way be considered as an admission that such prior art is widely known or forms part of the common general knowledge in the field.

Sterilisers are used in the medical, food and packaging industries to kill and thereby prevent the transmission of transmissible agents such as spores, fungi, and bacteria. A typical steriliser creates a set of physical conditions in a sterilisation chamber that effectively kills nearly all of these transmissible agents.

Contacting articles in need of sterilisation with sterilant aerosols is one known method of sterilisation. A typical aerosol sterilisation apparatus of the prior art has a sterilisation chamber with inlet and an outlet valves, an aerosol generator (typically a nebuliser) in fluid communication with the chamber via the inlet valve and a fan upstream of, and in fluid communication with, the aerosol generator.

In use, an article requiring sterilisation is placed in the chamber, which is then sealed. The aerosol inlet valve is opened and the outlet valve is closed. The fan is engaged, which creates a gas stream through or the past the aerosol generator, into the chamber. A passive vent in the sterilisation chamber allows for pressure equalization as required, to permit gas flow in and out of the sterilisation chamber. The aerosol generator, which contains the desired sterilant, is then activated, putting a large number of small sterilant droplets into gas stream. The droplets are carried by the gas stream to create an aerosol which travels into the sterilisation chamber. The sterilant concentration in the aerosol stream can be adjusted by changing either the flow rate of the gas stream, the productivity of the aerosol generator, or the concentration of the liquid sterilant used.

The passive waste vent allows some flow to pass through it, allowing the sterilisation chamber to remain at approximately room pressure. This passive system may include a pathway for flow to the outside air past catalytic elements that react with the sterilant and break the sterilant down into a safer chemistry suitable for disposal.

After a period of time, the fan and the aerosol generator are deactivated and the air inlet valve is closed, hence completing the sterilant delivery phase. The exit valve is then opened and aerosol is actively removed, typically by way of a pump that pulls aerosol and vapour out of the sterilisation chamber at a high rate. The removal system may include a pathway for flow between the sterilisation chamber and outside air past catalytic elements that react with the sterilant and break the sterilant down into a safer chemistry suitable for disposal. The passive vent allows a source of fresh air to be drawn into the sterilisation chamber from the outside air.

It is generally desirable for the total sterilisation cycle time to be as short as possible. Short reprocessing durations increases the number of times the sterilised article can be used in a given period, which in turn increases the number of patients per day that can be treated. In the case where the article to be sterilised is a high-cost medical device, short cycle times can generate significant financial savings for a health care provider.

One of the limitations of using an aerosol-based steriliser is that in order to gain the required level of microbiological reduction in a short sterilisation time a high concentration (i.e. a high mist density) of aerosol sterilant is required. During sterilisation, a high concentration of aerosol sterilant causes droplets to coalesce on the surface of the article. This can also lead to multilayer B.E.T.-like absorption on the surface of the sterilized article. Coalesced and absorbed droplets can be difficult to remove from the article at the end of the sterilisation process. Large levels of residual sterilant left on the sterilised article can be harmful to operators and patients and as such are undesirable in a fully automated sterilisation device. Maximum residual levels of sterilant may be defined by the relevant standards, where these exist, or by biocompatibility testing, common usage or other assessment.

While the residual sterilant may be removed by washing, this is an expensive feature to add to an automated sterilisation device, and requires sterile water and fresh water supplies that cannot always be easily obtained. Alternatively, it is also undesirable to have staff hand-washing articles, as this requires the use of safety apparatus which can be expensive (such as fume hoods), can take up valuable time and space and moreover increases the risk of harmful sterilant coming into contact with the operator.

A washing phase also requires a subsequent drying phase which adds considerably to apparatus turn-around times.

Another method for removing residual sterilant is through aeration. Residual removal and evaporation can be achieved by passing a gas stream over the article. Large coalesced droplets take some time to be removed by this process, and this can lead to long cycle times. Higher flow rates or larger suction devices can be used to speed this process, however these devices are often noisy, bulky, and expensive. Devices of this nature are often relegated to central sterilisation areas, adding handling time and effort required to move articles between patients and sterilisation machines, and increasing the total reprocessing time between patients.

It is known in the art that sterilisers often operate using two sterilisation cycles; a first cycle to gain a first 6 log reduction in microbes, followed by a second cycle to achieve a further 6 log reduction in microbes. Aerosol sterilisers that achieve this level of microbial reduction in a single cycle require long sterilisation durations with low sterilant concentrations; long aeration times to remove residual sterilant, or use a powerful waste removal system that is bulky, noisy and/or expensive.

It is desirable to provide an aerosol-based disinfection system that can meet desired microbiological efficacy targets, is fast in total cycle time (including sterilisation and residual removal), is small, low-noise, does not require a fresh water supply, and can be conveniently located close to patients.

As used herein, the term "concentration" is used to refer to the amount or volume of active sterilising agent (such as hydrogen peroxide) relative to the amount or volume of inert carrier fluid (usually water) present. The term can be used in relation to a bulk liquid, to an individual aerosol particle, or to a collective group of aerosol particles generally, although it is not necessary that all particles in an aerosol have the same concentration, for example, if an aerosol arises from two different sources or if an aerosol has been partially modified in space or time.

The term "density" in relation to an aerosol refers to the amount of the total volume that is filled with aerosol particles. The density is a measure of a combination of aerosol droplet volume and the number of aerosol droplets per unit volume. Larger droplets or a higher number of droplets per unit area will both increase aerosol density, whereas smaller droplets or fewer droplets per unit volume will both decrease aerosol density.

The dosage of sterilant delivered is a function of the concentration, the density and the delivery time.

SUMMARY OF THE INVENTION

According to a first aspect the invention provides a method of sterilising an object comprising the steps of:
i) placing an article to be sterilised in a sterilisation chamber;
ii) providing a sterilising mist to the sterilisation chamber, thereby to contact said article for a first duration;
iii) providing a gas flow to said chamber for a second duration, thereby to displace, where present, said sterilising mist and to remove, where present, condensed mist from said article; wherein the total reduction in micro organisms over a time period encompassing the first duration and the second duration is less than log 6; and wherein steps ii) and iii) are repeated at least once to achieve a predetermined sterilisation parameter.

The predetermined sterilisation parameter may be for example, a predetermined sum total of contact time between the sterilising mist and the article; a predetermined sum total of sterilising mist provided to the sterilisation chamber or a predetermined level of sterilisation.

As used herein, the term "remove" in relation to the condensed mist on an article, encompasses removal of all the condensed mist, or partial removal of the condensed mist to the point that the level of residual sterilant would be generally recognised to be safe to bring into contact with a patient.

According to another aspect the invention provides a method of sterilising an object comprising the steps of:
i) placing an article to be sterilised in a sterilisation chamber;
ii) providing a known amount of a sterilising mist to the sterilisation chamber thereby to contact said article for a time $t_n$
iii) providing a gas flow to said sterilisation chamber thereby to displace, where present, said disinfecting mist and to remove, where present, condensed mist from said article; wherein the total reduction in micro organisms over the time period $t_n$ is less than log 6; and wherein steps ii) and iii) are repeated q times to achieve a predetermined sum total of contact time, $\Sigma_1^q tn$, between the sterilising mist and the article.

According to another aspect the invention provides a method of sterilising an object comprising the steps of:
i) placing an article to be sterilised in a sterilisation chamber;
ii) providing a known amount of a sterilising mist to the sterilisation chamber thereby to contact said article for a time $t_n$
iii) providing a gas flow to said sterilisation chamber for a time $t_m$, thereby to displace, where present, said disinfecting mist and to remove, where present, condensed mist from said article, and where $t_n$ and $t_m$ are independently variable; wherein the total reduction in micro organisms over the time period $t_n$ is less than log 6; and wherein steps ii) and iii) are repeated q times to achieve a predetermined sum total of contact time, $\Sigma_1^q tn$, between the sterilising mist and the article.

Preferably the invention also provides including the step of
iv) providing a final gas flow to said chamber for a third duration ($t_f$) to reduce condensed mist residues, where present, to an acceptable level.

In another aspect, the invention provides apparatus for use in accordance with the methods set out in any one of preceding aspects of the invention.

In another aspect, the invention provides apparatus when used in accordance with the methods set out in any one of the preceding aspects of the invention.

The total reduction in micro organisms over any given single cycle will alone typically not be sufficient to achieve the final desired level of disinfection. However, it is preferable that the total reduction in micro organisms over a single sub-cycle $t_n+t_m$ is less than log 4. The total sterilization over all sub-cycles is preferably greater than log 6, more preferably greater than log 8 and even more preferably greater than log 12.

It is preferred that the total reduction in micro organisms sought and achieved per subcycle is less than 100%, particularly for HLD (High Level Disinfection) devices which ultimately achieve 6 log total reduction in micro organisms. For sterilizers, which ultimately achieve 12 log total reduction in micro organisms, it is preferred if the total reduction in micro organisms sought and achieved per subcycle is less than 100%, Alternatively, it is preferable that the total reduction in micro organisms over any given subcycle will be less than 75% of the total reduction sought, more preferably less than 50% of the total reduction and even more preferably less than 33% of the total reduction sought, when expressed logarithmically.

Preferably the sterilising mist is provided to the sterilising chamber at a controlled humidity. Preferably, the humidity is controlled to about 20 to 99%, and more preferably 40 to 70%

Preferably the sterilising mist is provided to the sterilisation chamber in a measured or predetermined dose. Preferably the sterilising mist is provided to the sterilisation chamber in a dose measured by measuring mist density, flow rate and time.

The mist is preferably provided to the sterilisation chamber in a square wave dosage pattern. Alternatively, the mist may be provided to the chamber in such a way that when mist delivery is on, it is held between predetermined upper and lower limits for a predetermined time, thereby allowing a close approximation to square wave delivery.

In one embodiment, the sterilant chamber inlet and outlet are the same fluid line.

Preferably the sterilant is hydrogen peroxide solution.

Preferably the sterilant concentration is kept constant for subsequent delivery phases. Alternatively, the sterilant concentration is varied for subsequent delivery phases.

Preferably the first duration ($t_n$) is kept constant for all sub-cycles. Alternatively, the first duration is varied for one or more sub-cycles Preferably the first duration is more than ten seconds and less than ten minutes, more preferably first duration is more than ten seconds and less than three minutes, and even more preferably the first duration is more than ten seconds and less than two minutes Preferably the second duration ($t_m$) is kept constant for all sub-cycles. Alternatively the second duration is varied for one or more sub-cycles Preferably the second duration is more than ten seconds and less than ten minutes, more preferably the second duration is more than ten seconds and less than three minutes and even more preferably, the second duration is more than ten seconds and less than two minutes Preferably the complete cycle duration is less than 30 minutes, and more preferably the complete cycle duration is less than 7 minutes. That is $$\Sigma_1^q tn + \Sigma_1^q tm + (optimally) \, tf$$

is less than 30 minutes, and more preferably, is less than 7 minutes.

Preferably there are three or more delivery and waste removal phases in a complete sterilisation cycle (i.e. preferably $q \geq 3$) where the microbial reduction is 12 log or greater.

Preferably there are two or more delivery and waste removal phases in a complete high level disinfection (HLD) cycle (i.e. preferably $q \geq 2$) where the microbial reduction is 6 log or greater.

Preferably, two or more delivery and waste removal phases are required to provide more than or equal to 6 log reduction in micro organisms and less than 12 log reduction in micro organisms.

Preferably, the liquid sterilant is 35% hydrogen peroxide solution.

The processes of the present invention are preferably carried out at atmospheric pressure or above.

In other embodiments of the invention, the invention may be carried out in such a way that the chamber is any enclosed space (such as a room) and the article to be sterilised is any surface within that space, for example, the walls, floor, operating tables etc.

BRIEF DESCRIPTION OF THE DRAWINGS

FIG. 3a is a schematic diagram of the relationship between aerosol flow into the chamber, total aerosol delivered to the article, and the amount of sterilant in the chamber at any given time using an ultrasonic nebuliser that provides a square wave dosage pattern (FIG. 3a).

FIG. 3c is similar to FIG. 3a, except that aerosol delivery is held between predetermined upper and lower limits for a predetermined time.

BRIEF DESCRIPTION OF THE INVENTION

The present invention employs the cyclic delivery and removal of sterilant during the sterilisation process. Surprisingly, it has been found that this method, which involves repeated sub-sterilisation and waste removal cycles, allows faster total sterilisation and waste removal durations than methods which aim to achieve the desired level of sterilisation in a single sterilisation step. The method of the present invention achieves faster total time by leaving lower levels of residual sterilant on the surface of articles to be disinfected once dispensing of the sterilant is complete. The lower initial level of residual means that additional drying time, if required at all, is reduced relative to the drying time that would be required if an equivalent sterilization was achieved by way of a single sterilisation cycle. Moreover, the method of the present invention is able to utilize devices that are smaller, faster and quieter than otherwise possible.

The method and apparatus of the present invention will be described in the context of the aerosol sterilisation apparatus illustrated in the accompanying drawings.

Figure 1:
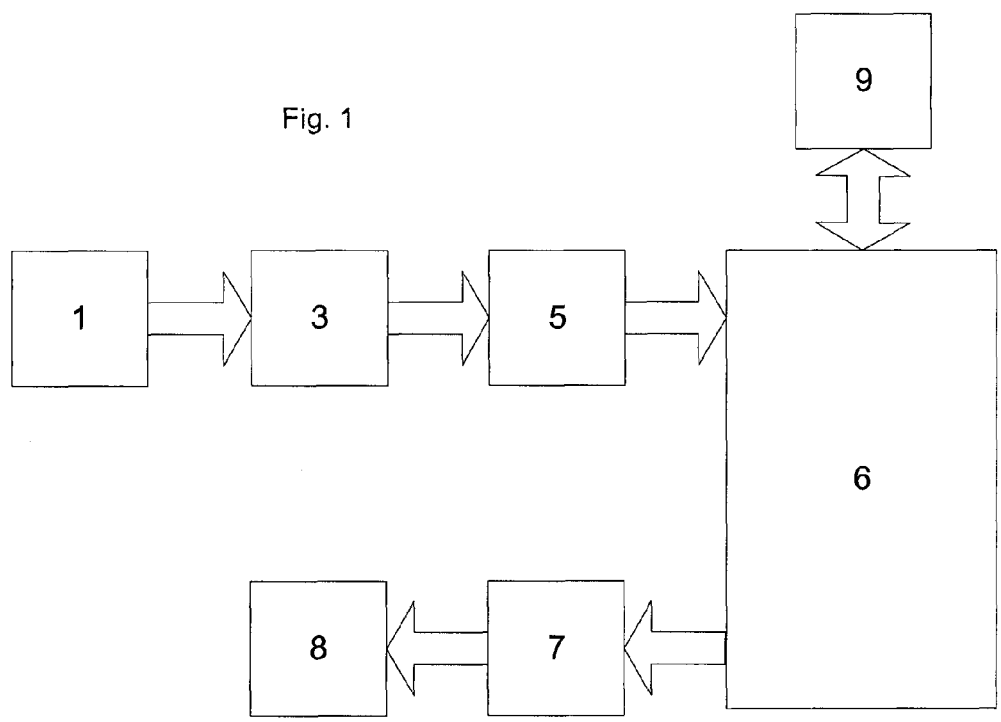
FIG. 1 is a schematic diagram of apparatus suitable for use in the present invention.

A schematic diagram of apparatus suitable for use in the present invention is shown in FIG. 1, however, it is conceivable that those in the art could use other aerosol sterilisation apparatus in accordance with the method described herein without deviating from the spirit of the present invention.

An article to be sterilised, such as an endoscope or the like, is placed by the operator into the sterilisation chamber 6. The chamber is then closed. During the sterilant delivery phase, the inlet valve 5 is opened and outlet valve 7 is closed. The fan 1 is engaged, generating a gas stream into the nebuliser 3. The nebuliser is, for preference, an ultrasonic nebuliser. A number of commercially available ultrasonic nebulisers are available which may be used in the present invention. The nebuliser 3 contains the liquid sterilisation agent, 35% hydrogen peroxide and is activated with the fan or shortly after the fan is turned on. The nebuliser generates droplets that are carried by the gas stream to create an aerosol which travels into the sterilisation chamber. The sterilant concentration in the aerosol stream can be adjusted by changing either the flow rate of the gas stream, the productivity of the nebuliser, or the concentration of the initial liquid sterilant that is nebulised. The passive waste removal vent or system 9 allows some gas flow to pass through it, equalising pressure and allowing the sterilisation chamber to remain at approximately room pressure. This passive system may typically include a pathway for flow to the outside air past catalytic elements that react with any sterilant and break the sterilant down into a safer chemistry suitable for disposal.

During the sterilant delivery phase, the aerosol droplets contact the surface of the article to be sterilised, as well as the inner surface of the chamber. The small size of the droplets, especially relative to their surface area, enables them to spread in a uniformly thin manner over the surface of the article, as well as access small areas, in some cases even mated surfaces.

At the end of the delivery phase, the fan 1 and the nebuliser 3 are deactivated and the air inlet valve 5 is closed. The exit valve 7 is opened and aerosol is removed with the active sterilant removal/waste system 8, which may include a pump that pulls aerosol and vapour out of the sterilisation chamber at a high rate. The gas flow removes unused aerosol from the chamber, and also removes aerosol from the surface of the article to be sterilised, and from the chamber walls. With the nebuliser off, the fan 1 may also be used to assist in the aerosol removal phase. This has the advantage of removing any unused and/or condensed aerosol from the aerosol delivery pathway. If the aerosol delivery pathway is kept dry and free from any material, such as residual peroxide, the measuring of subsequent doses of aerosol can be made with more confidence.

The removal system may include a pathway for flow between the sterilisation chamber and outside air past catalytic elements that react with the sterilant and break the sterilant down into a safer chemistry suitable for disposal. Passive vent 9 allows a source of fresh air to be drawn into the sterilisation chamber from the outside air.

The switching of the various components of the apparatus is generally under software control, to ensure appropriate operation of the fan, nebuliser and valves in correct order, and to ensure that the timing is accurately controlled. The device may also incorporate flow sensors in line between the nebuliser and sterilising chamber and/or liquid level sensors in the nebuliser to measure when predetermined levels of sterilant have been administered to the chamber or used by the nebuliser. Additionally, the surface of the sterilisation chamber may be electronically heated to a controlled temperature by thermostat means or otherwise, hence accelerating the speed of sterilisation.

Figure 2:
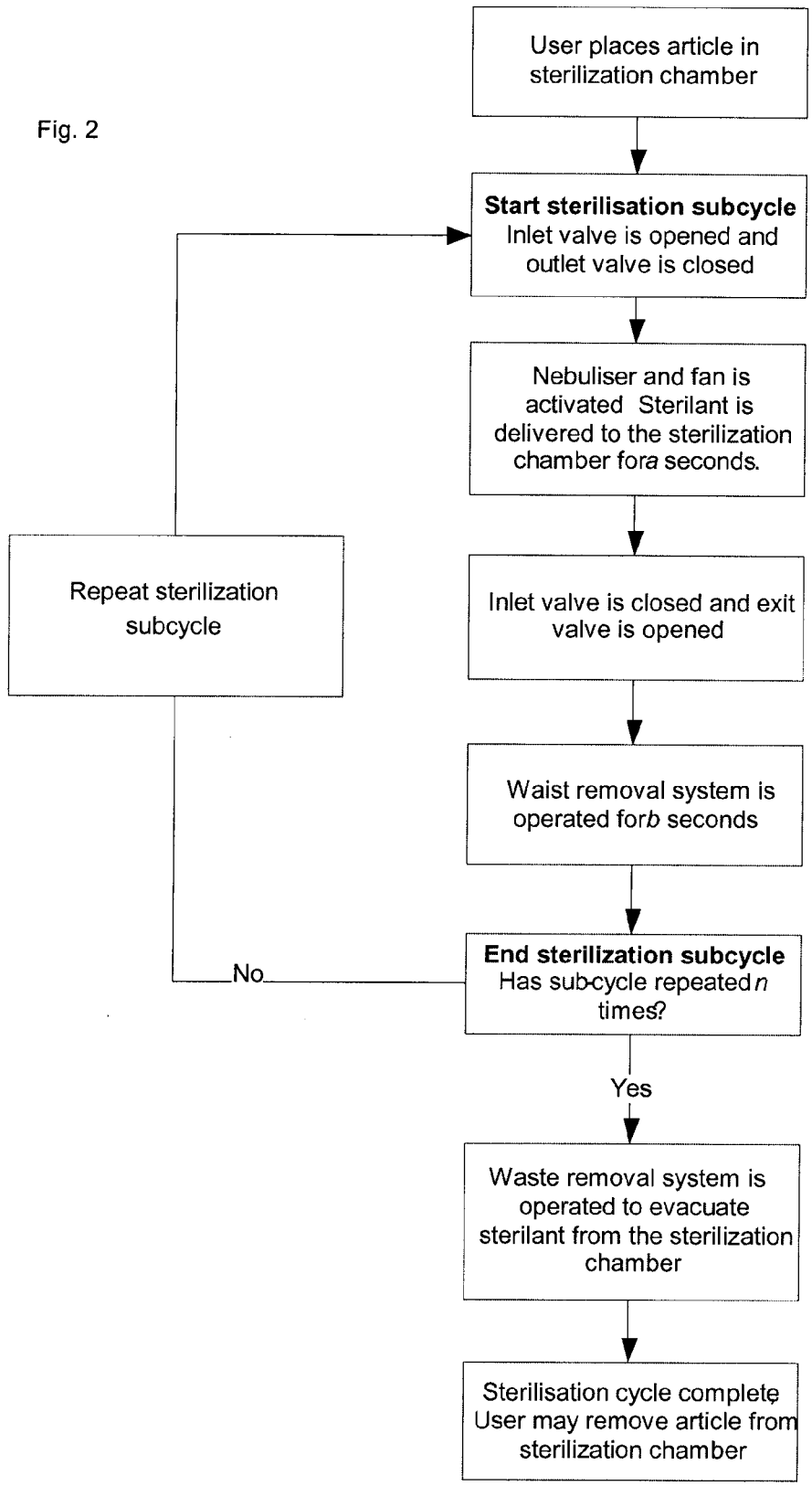
FIG. 2 is a schematic diagram of the method of the present invention.

The method of the present invention is more particularly illustrated in FIG. 2. The sterilisation method of the present invention is broken up into a number of short sub-cycles, where each sub-cycle consists of a sterilant delivery phase and a waste removal phase. Sub-cycles are repeated a number of times until at least one of the following conditions is met:
i) the desired total sterilant contact time is achieved,
ii) a desired amount of sterilant has been dispensed or metered into the chamber; or
iii) a desired reduction in microbial load has been achieved
iv) all required aspects of a certified sterilisation procedure have been fulfilled.

The sub cycles may be repeated as many times as needed to achieve the desired outcome. Each sub-cycle may be identical in terms of the duration $t_n$ of the delivery phase and removal phase, or it may vary independently, for example using increasingly longer or shorter cycles as the sterilisation progresses.

In one preferred embodiment, the delivery phase operates between about 10 seconds and two minutes (i.e. $10 \text{ s} < t_n < 120 \text{ s}$) although it may typically be as long as 10 minutes (i.e. $10 \text{ s} < t_n < 600 \text{ s}$).

Any number of cycles may be employed, but typically around 2 to 10 ($2 < q < 10$) cycles, and more usually three ($q=3$) cycles are employed.

Total contact time between the sterilant aerosol and the article to be sterilised is the sum of all delivery phases over the total number of sub-cycles. In use, this total time $\Sigma_1^q tn$ can be predetermined by correlating the times with known parameters to achieve a desired outcome.

Alternatively, the process can be operated to either dispense a predetermined or measured amount of sterilising agent, or to provide a predetermined or measured amount of aerosol into a chamber.

The liquid level in the nebuliser can be monitored and the total amount dispensed can be measured, if necessary with feedback to the device to switch off the nebuliser when a predetermined level of liquid has been consumed.

More preferably, however, the flow rate and mist density into the chamber are measured, which gives an indication of the amount of aerosol delivered. Given sterilant concentration is known, then measuring the aerosol density, rate of flow into the chamber, and time of flow into the chamber, then the amount of sterilant dispensed to the chamber in any sub-cycle can be calculated. The amounts delivered in each sub-cycle can be added to provide an indication of the total amount delivered to the article over the whole sterilisation process.

Figure 3B:
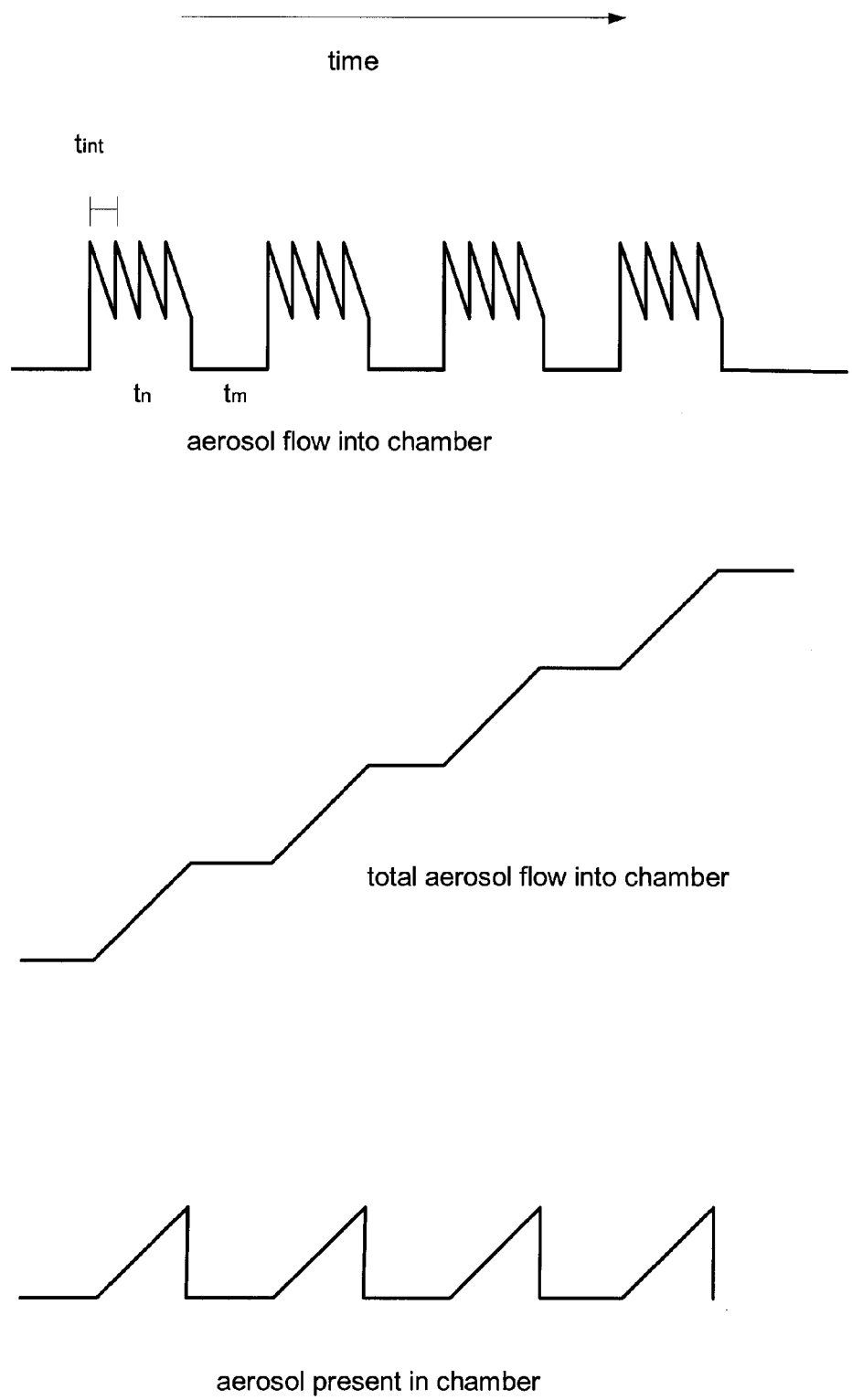
FIG. 3b is similar to FIG. 3a, except that aerosol delivery is from a nebuliser that pulses on and off with a frequency of $t_{int}$ during each delivery sub-cycle (FIG. 3b)

FIG. 3 shows a schematic diagram of the relationship between aerosol flow into the chamber, total aerosol delivered to the article, and the amount of sterilant in the chamber at any given time The aerosol flow into the chamber is typically by means of a ultrasonic nebuliser that provides a square wave dosage pattern (FIG. 3a). Alternatively, the aerosol delivery is from a nebuliser that pulses on and off with a frequency of $t_{int}$ during each delivery sub-cycle (FIG. 3b). By controlling the ratio of pulse durations and the total duration of on pulses during each delivery cycle it is possible to control the amount of aerosol dispensed into the gas flow.

As a further alternative, the mist can be provided to the chamber in such a way that the delivery rate is held between predetermined upper and lower limits for a predetermined time (FIG. 3c). In that way, an estimation of total dosage range can be established.

The total amount of aerosol delivered to the chamber is gradually stepped up, whilst the total amount of sterilant in the chamber at any given instant is quite low.

The process parameters can also be used to achieve a predetermined level of sterilisation at each sub-cycle, and overall. This is important if certification of sterilisation is to be achieved. Certification means establishing operating parameters for each device which reproducibly ensure a defined outcome—the benefit being that articles can be certified as sterile if certain parameters are employed without the need for repeated and impracticable biological testing at each stage.

In the present example, a variety of parameters are tested to establish microbial reductions in a single cycle and multiple cycles. These parameters can simply be preset into the apparatus and a subsequent operator only need to select the desired outcome. For example, parameters are tested such that a measured >log 4 reduction in microbial load is achieved in a single cycle. That cycle can be repeated to give a >log 8 reduction or repeated twice to provide a >log 12 reduction. The result can then be certified as a log 12 reduction in bacteria.

Delivery phase sub-cycle times are determined based on sterilant aerosol concentration and the rate of droplet coalescence on the surface of the article. Preferably, the sterilant aerosol concentration and contact time are chosen such that there is significant microbial reduction without creating large coalesced droplets within the sterilisation chamber. This allows the waste removal phase to be performed in a short duration utilizing a small, low-noise and low-cost fan system. The length of the waste removal phase is determined by the efficiency of the waste removal system.

The aerosol removal phase $t_m$, is also important, as it needs to be sufficient in conjunction with the gas flow to remove the aerosol, and also dry the surface of the article to be sterilised. It is not desirable to run the removal phase of each sterilising sub-cycle for any longer than necessary, since that simply adds to total cycle time. However, an additional waste removal phase is preferably provided at the end of the cycle to provide extra safety margin in the removal of residual sterilant.

Both the delivery and waste removal sub-cycle parameters can be optimised for particular applications. Larger sterilisation chambers will normally require longer delivery sub-cycles in order for the sterilant aerosol concentration and distribution to reach desired levels. Similarly, larger chambers may take longer for the waste removal phase to complete.

Tests were performed comparing the performance of the method of the present invention with a well-known single cycle method using the same sterilisation apparatus. In the single cycle method the chamber humidity was maintained approximately constant for the entire cycle. Settings were chosen in order to achieve >6 log reduction of *Staphylococcus Aureus* in both cases. A 5 minute total cycle time was used. A cleaned and dried medical device (L11-5 Ultrasound Transducer) was placed into the sterilization chamber and sterilant residuals were extracted from the surface of the medical device at the completion of each process. It was found that the residual sterilant on the medical device at the end of the process was approximately 5 times higher for the single cycle case when compared with the method of the present invention. Additionally, for the single cycle case only, it was found that residual sterilant droplets could be seen on the surface of the medical device after the completion of the process, and that this level of residue is considered unsafe for both operators and patients. Hence it can be seen that the method of the present invention provides a clear advantage in terms of the residue levels present at the end of the process.

The sterilisation system of the present invention also provides advantages in microbial efficiency. It is known that when certain microbes (such as *Candida Albicans* and *Staphylococcus Aureus*) come into contact with hydrogen peroxide sterilant a chemical reaction takes place that result in microbial reduction and the creation of water. Without wishing to be bound by theory, it is believed that the water forms a layer that can create a barrier, diluting fresh sterilant and preventing fresh sterilant droplets from reaching the microbes, and resulting in a reduction of sterilisation efficacy. The present invention removes this water layer during the waste removal phase, allowing fresh sterilant droplets to be delivered directly to the microbes, hence providing a more efficacious sterilisation process. To the surprise of the inventor, tests indicated that the delivery of a larger dosage of aerosol hydrogen peroxide sterilant was not as effective at sterilising *Candida Albicans* and *Staphylococcus Aureus* as was the cyclical process of the present invention. This was found to be particularly prevalent when a large number of microbes were layered onto a small surface area, as the build up of water from microbial reduction of the top layers makes it more difficult for fresh sterilant to reach the lower layers. This was also found to be particularly prevalent when the organisms were placed on a rough surface.

Some of the advantages of the present invention can be demonstrated by comparing experimental results for a triple-subcycle method of the present invention with the well-known single cycle method, both methods utilising the same total cycle time (5 minutes) and optimum sterilant concentrations. The organisms used were *Candida Albicans* and *Staphylococcus Aureus* placed on a textured surface (frosted glass slides). The results from these tests are presented in Table 1.

TABLE 1

| Organism | Log reduction after exposure to single cycle (average of 6 samples) | Log reduction after exposure to triple cycle (average of 6 samples) |
| --- | --- | --- |
| *Candida Albicans* (5 log control) | 2.6 | >5 (no surviving organisms) |
| *Staphylococcus Aureus* (7.2 log control) | <2.0 | 6.5 |

Tests were also performed to verify efficacy of the method of the present invention with spores *G. stearothermophilus* ATCC 7953. Of the six samples tested it was found that in all cases there was greater than 6 log reduction.

The method of the present invention can provide similar microbial reduction in a number of very short delivery phases, where each delivery phase is preferably less than two minutes, and each waste removal phase is preferable less than three minutes.

It has been found to be important to maintain humidity levels inside the steriliser system, and in particular, inside the sterilisation chamber. The reason for this is the high level of sensitivity of peroxide vapour density to humidity. The maximum concentration (indicative only) of hydrogen peroxide vapour/per cubic meter (peroxide density) at varying temperatures and relative humidities ("RH") is shown in Table 2:

TABLE 2

| | Max. peroxide vapour concentration using initial 35% $H_2O_2$ solution (mg/litre) | | | |
| --- | --- | --- | --- | --- |
| Temperature (° C.) | 10% RH | 20% RH | 40% RH | 80% RH |
| 20 | 0.97 | 0.85 | 0.62 | 0.14 |
| 40 | 4.13 | 2.59 | 2.66 | 0.63 |
| 60 | 14.4 | 12.60 | 9.1 | 2.31 |

At low relative humidities, the vapour concentration of peroxide is very high, that is, it equilibrates away from liquid (i.e. droplet or aerosol) form in dry air to gaseous form, whereas in less moist air, the peroxide is more likely to remain in the liquid (i.e. droplet of aerosol) form, rather than vaporising. However, moist air can lead to water condensing on surfaces, thereby providing a water barrier, making the surfaces more difficult for the peroxide to access. Thus, it is desirable to control relative humidity to levels between, for preference, 20 to 99%, and more preferably 40 to 70%, in order to minimise peroxide vaporisation whilst at the same time preventing surfaces from becoming wet.

To demonstrate the effectiveness of the sub-cycle based disinfection method of the present invention, an experiment was conducted to compare it to a prior-art disinfection cycle. Both disinfection cycles were carried out at the same required temperatures, using the same hydrogen peroxide sterilant aerosol dosages and aerosol contact durations in order to achieve 6 log reduction of bacteria.

The prior art disinfection cycle consisted of one contact phase between the sterilant and the article followed by a remediation phase to provide a total cycle time of 7 minutes. The disinfection cycle of the present invention consisted of two equal contact phases between the sterilant and the article separated by a short remediation phase, followed by a final remediation phase to provide a total cycle time of 7 minutes. Total contact time was the same in both cases.

Two probes of different construction (an intracavity probe and a surface ultrasound probe) were chosen as the articles for disinfection. Each was subjected to both the prior art method and the method of the present invention.

At the conclusion of each disinfection cycle, each probe was tested for residual sterilant. Each disinfection cycle type was tested twice with each probe, and results were averaged. It was discovered that residue levels present on the probes after the prior-art disinfection cycle were 150% (surface probe) and 342% (intracavity probe) of the residue levels on the same probes after the disinfection cycle of the present invention.

It was also found that the disinfection cycle of the present invention provided a residue level on the surface of the ultrasound transducer that was safe for users to touch with bare skin, however the prior-art disinfection cycle residue levels contained unsafe levels of residue that could sometimes be visually seen as droplets formed on the surface of the probe. These experiments clearly indicate the advantages of using the sub cycle disinfection methods of the present invention.

References to sterilisation and disinfection within this document are also intended to include other levels of microbial reduction, including but not limited to sterilisation, high and low level disinfection. In the case where high level disinfection is being referred to specifically, the acronym HLD is used.

References to "remove", "removal", "removing" and the like include the all possibilities in the range of partial removal to complete removal. Hence, references to the removal of sterilant are intended to mean the removal of at least some sterilant or the removal of all sterilant.

The term "mist" also means "aerosol", and the two terms are used interchangeably herein.

References to "reduction in microbes" or "reductions in micro organisms" are intended to mean the reduction in population of a single test sample of a single test organism. A reduction of greater than 6 log (1 million) is intended to mean that a single carrier loaded with an initial population of 6 log or greater test organisms will have its total population reduced by 6 log (1 million) or more. Test organisms include (but are not limited to) those organisms used for international regulatory approval of disinfection and sterilisation products.

References to microbial reductions specified of greater than 6 log are also intended to mean the sum of the 6 log reduction plus a sterility assurance level (SAL) corresponding to the additional amount of the reduction specified above 6 log reduction. Hence a reference to greater than or equal to 9 log reduction is also meant to include a greater than or equal to 6 log reduction plus a greater than or equal to 3 log SAL.

References to 12 log reduction also mean a theoretical 12 log reduction. It is common in the industry to demonstrate 12 log reduction (albeit theoretically) by achieving greater than or equal to 6 log reduction in a first duration in a sterilizer, then sequentially subjecting the article to the same conditions for a second duration. This second duration is often called the "overkill" cycle, and provides a 6 log SAL. Hence references to greater than or equal to 12 log reduction are also intended to mean greater than or equal to 6 log reduction with a greater than or equal to 6 log SAL.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The claims defining the invention are as follows:

1. A method of sterilizing an object to achieve 6 log or greater total reduction in micro organisms comprising the steps of:
   i) placing an article to be sterilized in a sterilization chamber;
   ii) providing, in a delivery phase of a sub-cycle, a sterilizing mist of liquid droplets of sterilant in a gas to the sterilization chamber at atmospheric pressure or above, thereby to contact said article for a first duration; and
   iii) providing, in a waste removal phase of the sub-cycle, a gas flow to said chamber for a second duration, thereby to displace, where present, said sterilizing mist and to remove, where present, condensed mist from said article and to dry the surface of the article to be sterilized; wherein the total duration encompassing the first duration and the second duration is specifically selected in order to produce a total reduction in micro organisms to be less than 6 log;
   wherein the sub-cycle is repeated at least once to achieve a predetermined sum total of sterilizing provided to the sterilization chamber, or a predetermined level of sterilization.

2. A method according to claim 1, further comprising the step of iv) providing a gas flow to said chamber for a third duration to reduce condensed mist residues, where present, to an acceptable level.

3. A method according to claim 1, wherein the total reduction in micro organisms over a time period encompassing the first duration and the second duration is less than log 4.

4. A method according to claim 1, wherein the sterilizing mist is provided to the sterilizing chamber at a controlled humidity.

5. A method according to claim 1, wherein the sterilizing mist is provided to the sterilization chamber in a measured or predetermined dose.

6. A method according to claim 5, wherein the sterilizing mist is provided to the sterilization chamber in a dose measured by measuring mist density, flow rate, time.

7. A method according to claim 1, wherein the sterilizing mist is provided to the sterilization chamber in a predetermined dose.

8. A method according to claim 1, wherein the sterilizing chamber inlet and outlet are a same fluid line.

9. A method according to claim 1, wherein a sterilant is hydrogen peroxide solution.

10. A method according to claim 1, wherein sterilant concentration is kept constant for subsequent delivery phases of the sterilizing mist.

11. A method according to claim 1, wherein sterilant concentration is varied for subsequent delivery phases of the sterilizing mist.

12. A method according to claim 1, wherein the first duration is kept constant for all sub-cycles comprising the delivery phase.

13. A method according to claim 1, wherein the first duration is varied for one or more sub-cycles comprising the delivery phase.

14. A method according to claim 1, wherein the first duration is more than ten seconds and less than ten minutes.

15. A method according to claim 1, wherein the first duration is more than ten seconds and less than three minutes.

16. A method according to claim 1, wherein the first duration is more than ten seconds and less than two minutes.

17. A method according to claim 1, wherein the second duration is kept constant for all sub-cycles comprising the waste removal phase.

18. A method according to claim 1, wherein the second duration is varied for one or more sub-cycles comprising the waste removal phase.

19. A method according to claim 1, wherein the second duration is more than ten seconds and less than ten minutes.

20. A method according to claim 1, wherein the second duration is more than ten seconds and less than three minutes.

21. A method according to claim 1, wherein the second duration is more than ten seconds and less than two minutes.

22. A method according to claim 1, wherein a complete cycle duration of the repeated steps is less than 30 minutes.

23. A method according to claim 1, wherein a complete cycle duration of the repeated steps is less than 7 minutes.

24. A method according to claim 1, wherein there are three or more sterilizing mist and gas flow providing cycles in a complete sterilization cycle wherein there is equal to or greater than 12 log reduction in micro organisms.

25. A method according to claim 1, wherein two or more sterilizing mist and gas flow providing cycles are required to provide equal to or more than 6 log reduction in micro organisms and less than 12 log reduction in micro organisms.

26. A method according to claim 1, wherein the chamber is any enclosed space and the article to be sterilized is any surface within that space.

27. A method according to claim 26, wherein the chamber is a room.

* * * * *